(12) United States Patent
von Gutfeld et al.

(10) Patent No.: US 10,456,515 B2
(45) Date of Patent: Oct. 29, 2019

(54) WEARABLE ULTRAFILTRATION DEVICES METHODS AND SYSTEMS

(71) Applicant: The Trustees of Columbia University in the City of New York, New York, NY (US)

(72) Inventors: Robert J. von Gutfeld, New York, NY (US); Arthur Autz, Douglaston, NY (US); Edward F. Leonard, Bronxville, NY (US); Stanley Cortell, Bronxville, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/058,542

(22) Filed: Aug. 8, 2018

(65) Prior Publication Data

US 2018/0344914 A1    Dec. 6, 2018

Related U.S. Application Data

(63) Continuation-in-part of application No. 15/615,541, filed on Jun. 6, 2017, now abandoned.
(Continued)

(51) Int. Cl.
*A61M 1/16* (2006.01)
*A61M 1/34* (2006.01)
(Continued)

(52) U.S. Cl.
CPC ............ *A61M 1/1633* (2014.02); *A61M 1/34* (2013.01); *A61M 1/3479* (2014.02);
(Continued)

(58) Field of Classification Search
CPC .... A61M 1/1633; A61M 1/34; A61M 1/3479; A61M 1/3626; A61M 2205/8206;
(Continued)

(56) References Cited

U.S. PATENT DOCUMENTS

| 3,388,803 A | 6/1968 | Scott |
| 3,902,490 A | 9/1975 | Jacobsen et al. |

(Continued)

FOREIGN PATENT DOCUMENTS

EP    2281591 A1    2/2011

OTHER PUBLICATIONS

Armignacco et al., "Pumps in Wearable Ultrafiltration Devices: Pumps in Wuf Devices," Blood Purification (2015); 39:115-124; DOI: 10.1159/000368943; published online Jan. 20, 2015 (10 pages).
(Continued)

*Primary Examiner* — Pranav N Patel
(74) *Attorney, Agent, or Firm* — McCarter & English, LLP

(57) ABSTRACT

A wearable ultrafiltration apparatus is provided. The apparatus can include a first ultrafilter for filtering a patient's blood along a first fluid path and a second ultrafilter for filtering the patient's blood along a second fluid path. The apparatus can also include a valve being positionable in a first position for directing the patient's blood along the first fluid path. The valve can also be positioned in a second position for directing the patient's blood along the second fluid path. When the valve is in the first position, blood can flow along the first fluid path and prevent blood from flowing along the second fluid path. When the valve is in the second position, blood can flow along the second fluid path and prevent blood from flowing along the first fluid path. When the valve is in the first position, the second ultrafilter
(Continued)

Front View can be idle and capable of being serviced or replaced and when the valve is in the second position, the first ultrafilter can be idle and capable of being serviced or replaced. Therefore, when a ultrafilter fouls, blood can be directed to the other ultrafilter while the fouled ultrafilter is being serviced or replaced.

7 Claims, 12 Drawing Sheets

Related U.S. Application Data

(60) Provisional application No. 62/346,404, filed on Jun. 6, 2016.

(51) Int. Cl.
| | | |
|---|---|---|
| *A61M 39/28* | (2006.01) | |
| *A61M 39/10* | (2006.01) | |
| *A61M 5/142* | (2006.01) | |
| *A61M 1/36* | (2006.01) | |
| *A61M 39/22* | (2006.01) | |

(52) U.S. Cl.
CPC ........ *A61M 5/14232* (2013.01); *A61M 39/10* (2013.01); *A61M 39/28* (2013.01); *A61M 1/3626* (2013.01); *A61M 2039/229* (2013.01); *A61M 2205/8206* (2013.01); *A61M 2209/088* (2013.01)

(58) Field of Classification Search
CPC ............ A61M 2209/088; A61M 39/10; A61M 39/28; B01D 61/28; B01D 61/30; B01D 61/32; B01D 27/142; B01D 27/144; B01D 2317/04
See application file for complete search history.

(56) References Cited

U.S. PATENT DOCUMENTS

| | | | |
|---|---|---|---|
| 4,235,231 A | 11/1980 | Schindler et al. | |
| 4,317,725 A | 3/1982 | Kume et al. | |
| 4,765,907 A | 8/1988 | Scott | |
| 4,950,230 A * | 8/1990 | Kendell | A61M 1/28 137/625.41 |
| 5,284,470 A | 2/1994 | Beltz | |
| 5,415,532 A | 5/1995 | Loughnane et al. | |
| 5,944,684 A | 8/1999 | Roberts et al. | |
| 6,117,100 A * | 9/2000 | Powers | A61M 1/16 210/645 |
| 6,960,179 B2 | 11/2005 | Gura | |
| 7,309,323 B2 | 12/2007 | Gura et al. | |
| 7,597,677 B2 | 10/2009 | Gura et al. | |
| 7,645,253 B2 | 1/2010 | Gura et al. | |
| 7,854,718 B2 | 12/2010 | Gura et al. | |
| 7,918,993 B2 | 4/2011 | Harraway | |
| 8,012,118 B2 | 9/2011 | Curtin et al. | |
| 8,034,161 B2 | 10/2011 | Gura et al. | |
| 8,349,174 B2 | 1/2013 | Bedingfield et al. | |
| 8,715,221 B2 | 5/2014 | Curtin et al. | |
| 8,741,131 B2 | 6/2014 | Bedingfield et al. | |
| 2005/0115898 A1* | 6/2005 | Sternby | A61M 1/16 210/636 |
| 2009/0120864 A1 | 5/2009 | Fulkerson et al. | |
| 2010/0170848 A1* | 7/2010 | Brunsman | A61M 1/0281 210/637 |
| 2011/0105982 A1 | 5/2011 | Leonard et al. | |
| 2013/0168303 A1* | 7/2013 | Appling | A61M 1/3626 210/95 |
| 2014/0138294 A1 | 5/2014 | Fulkerson et al. | |
| 2014/0217020 A1* | 8/2014 | Meyer | A61M 1/16 210/636 |
| 2014/0251908 A1 | 9/2014 | Ding et al. | |
| 2017/0368250 A1 | 12/2017 | Von Gutfeld et al. | |

OTHER PUBLICATIONS

Flythe et al., "Rapid fluid removal during dialysis is associated with cardiovascular morbidity and mortality," Kidney International (2011) 79, 250-257; doi:10.1038/ki.2010.383; published online Oct. 6, 2010 (8 pages).

Gura et al., "A wearable artificial kidney for patients with end-stage renal disease," JCI Insight (2016) 1(8):e86397; doi:10.1172/jci.insight.86397; published online Jun. 2, 2016 (15 pages).

Gura et al., "A wearable hemofilter for continuous ambulatory ultrafiltration," Kidney International (2008) 73, 497-502; doi:10.1038/sj.ki.5002711; published online Dec. 5, 2007 (6 pages).

Marenzi et al., "Continuous Ultrafiltration for Congestive Heart Failure: The CUORE Trial," Journal of Cardiac Failure (2014); 20(5):378.e1-9; DOI: 10.1016/j.cardfail.2014.04.004; published May 2014 (10 pages).

Ronco et al., "Hydrodynamic Analysis of the Miniaturized Hemofilter for a Wearable Ultrafiltration Device," Blood Purification (2013); 35:127-132; DOI: 10.1159/000346098; published online Jan. 22, 2013 (6 pages).

Invitation to Pay Additional Fees dated Jun. 13, 2019, issued in connection with International Application No. PCT/US2019/030046 (2 pages).

International Search Report and Written Opinion of the International Searching Authority, dated Aug. 23, 2019, in connection with International Application No. PCT/US2019/030046 (10 pages).

* cited by examiner

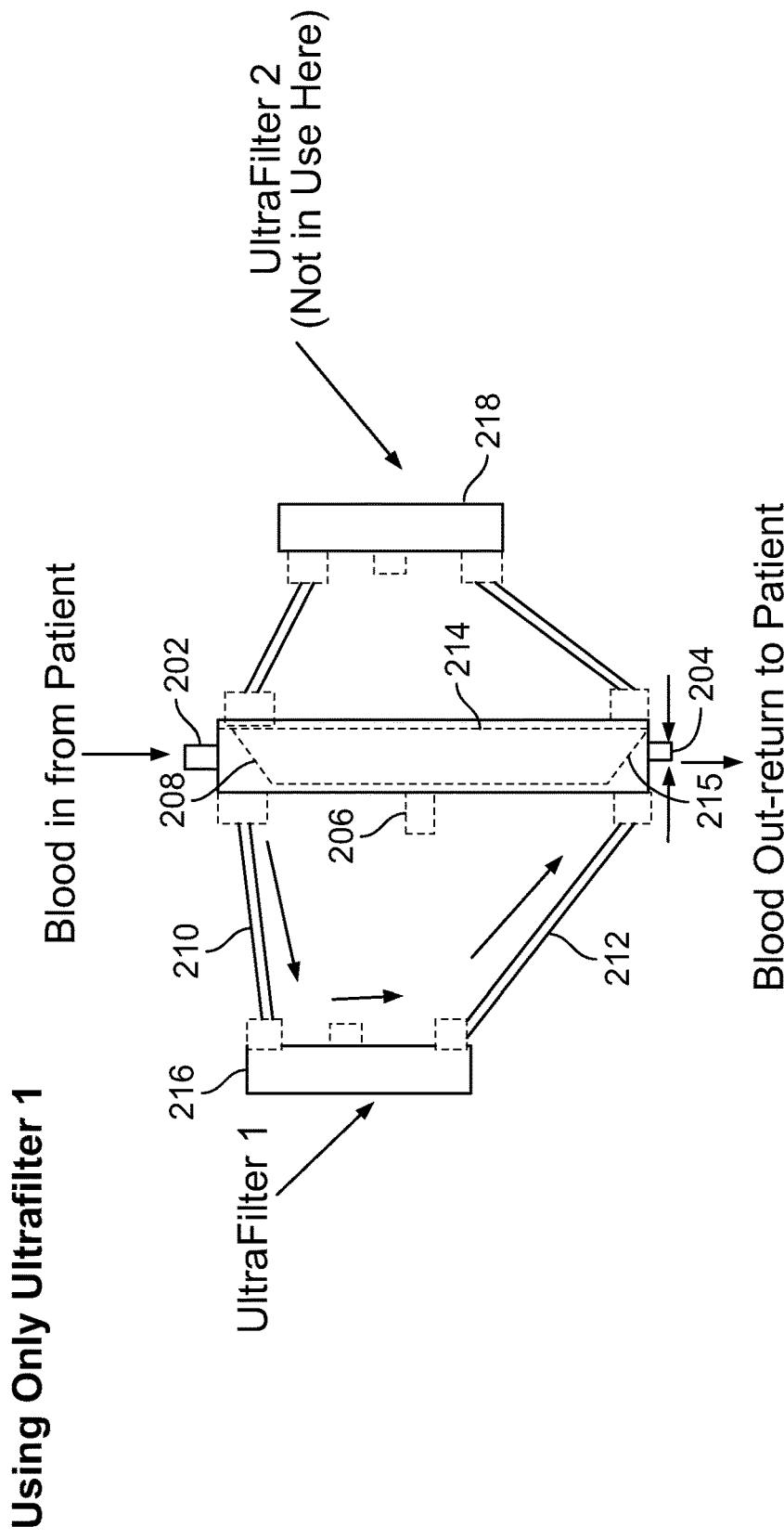

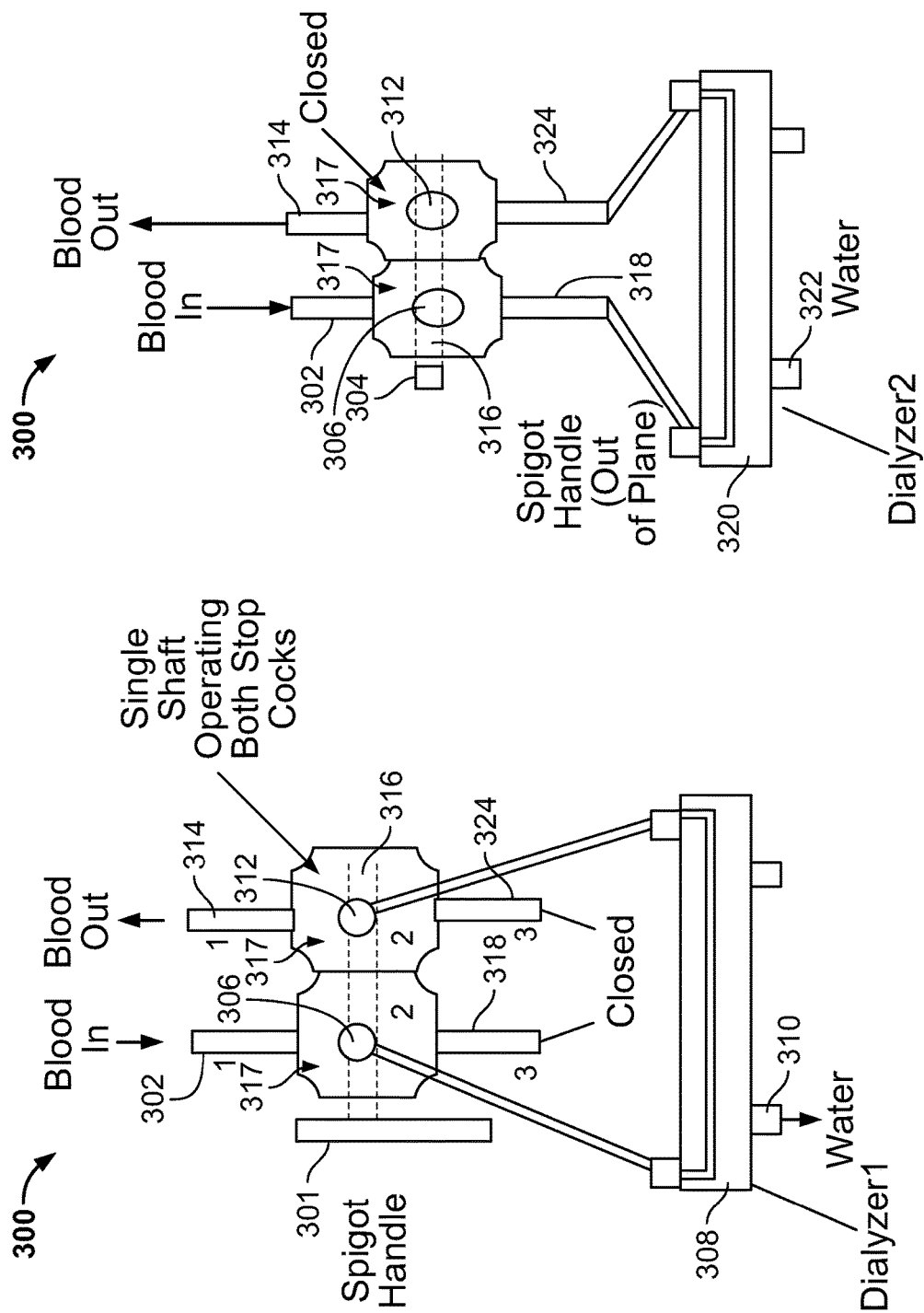

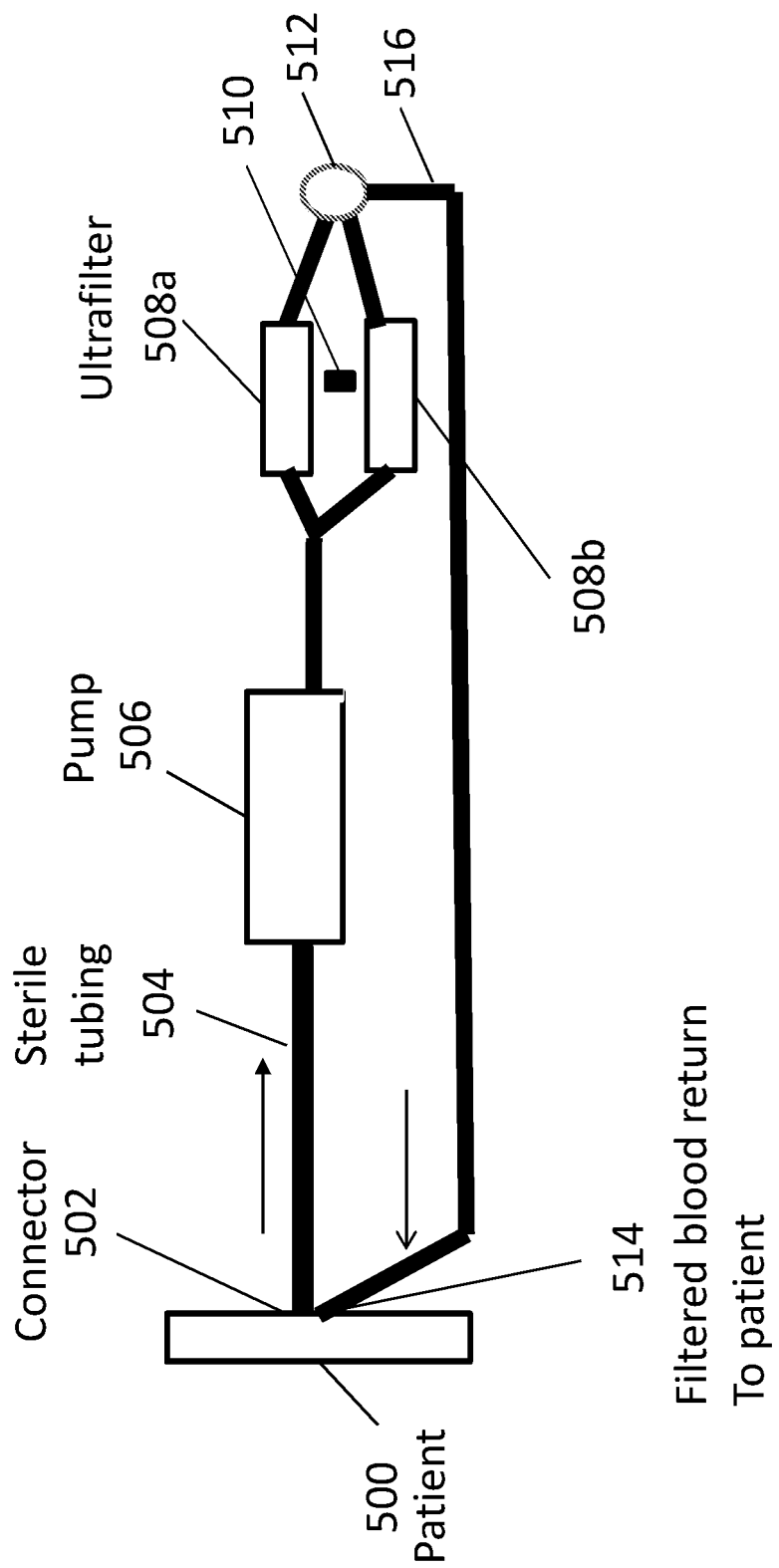

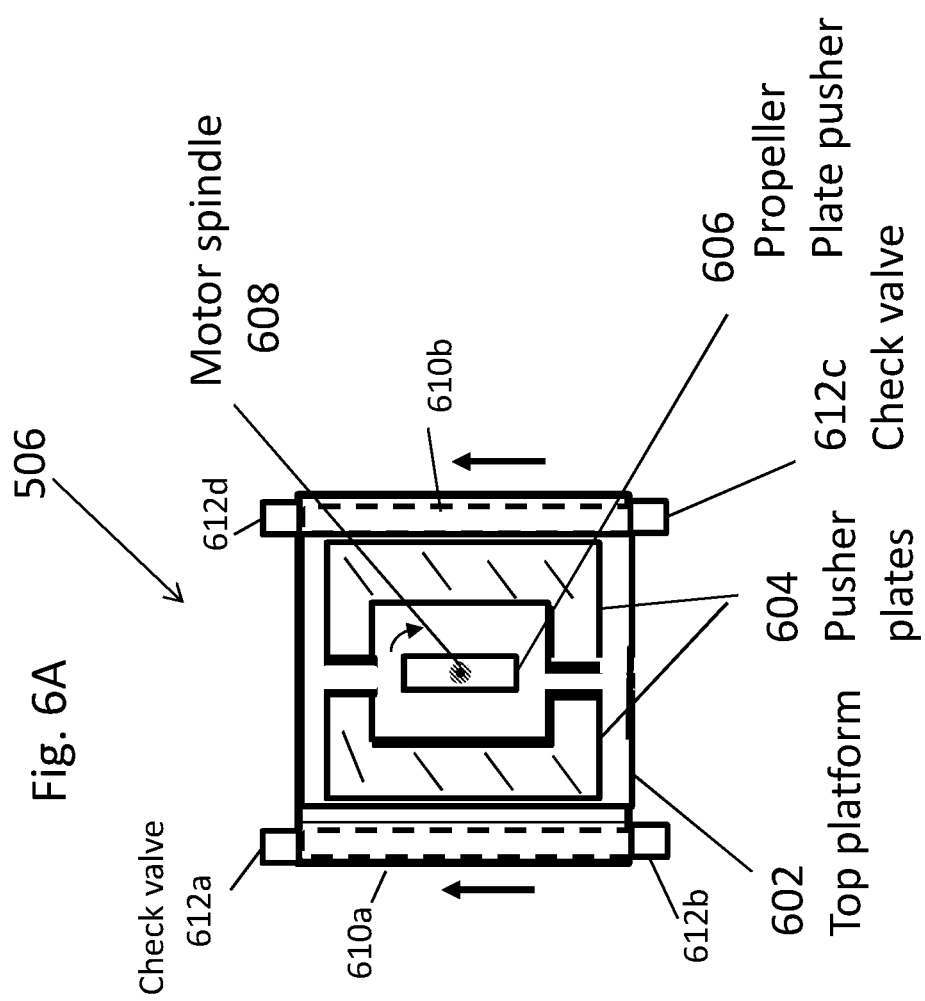

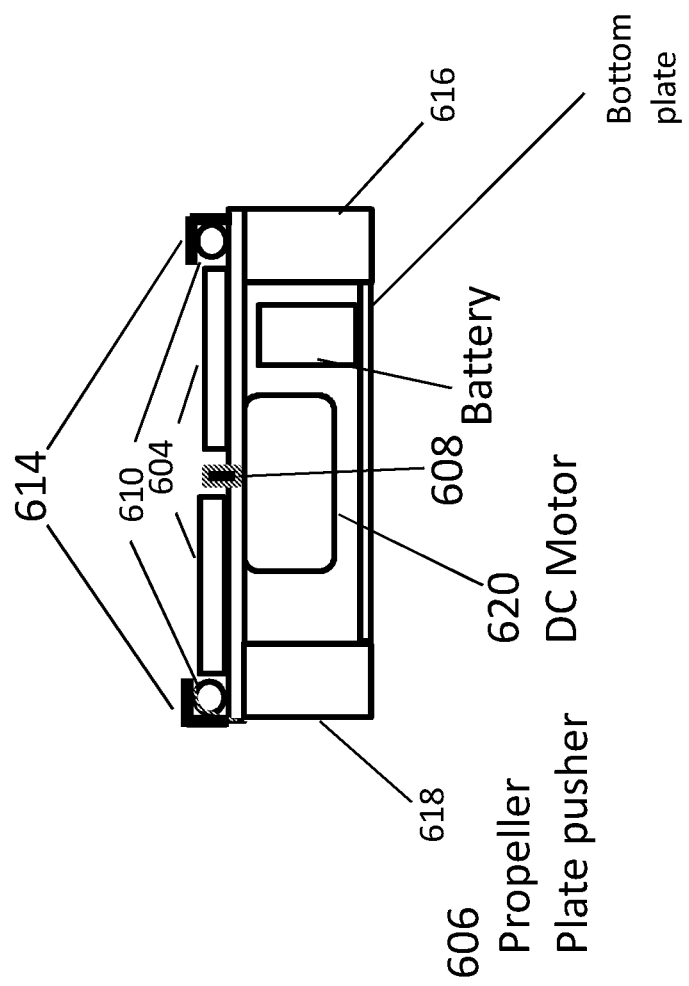

WEARABLE ULTRAFILTRATION DEVICES METHODS AND SYSTEMS

RELATED APPLICATIONS

This application is a continuation-in-part of U.S. patent application Ser. No. 15/615,541 filed Jun. 6, 2017, which claims priority to U.S. Provisional Patent Application Ser. No. 62/346,404 filed on Jun. 6, 2016, the entire disclosures of which are hereby incorporated by reference.

BACKGROUND

Field of the Disclosure

The present disclosure relates to a wearable device for removing unwanted waste products from a person's blood. More particularly, the present disclosure relates to wearable ultrafiltration devices, methods, and systems.

Related Art

When treating patients with inadequate kidney function, it is highly desirable to remove excess metabolites, especially water, in a slow, continuous fashion, thus stabilizing blood volume and pressure. A wearable removal system permits continuous processing without confining the patient to the clinic. However, wearable removal systems or metabolite-removing devices, such as dialyzers or ultrafilters, have short operating times due to the mechanical and chemical complexity needed to fully replace kidney function and to store materials removed from the blood. Present treatments provide efficient removal of toxins from blood in typically 3 treatments per week each of about 3 hours duration leaving the patient untreated for more than 90% of the time, which is both unhealthy and profoundly uncomfortable. Interventions applied between present treatments must both be effective and reduce the time during which no treatment is provided.

It is particularly desirable to maintain volume homeostasis in a patient by continuous removal of water containing only the small solute molecules in blood. This is commonly achieved in the kidney by filtration through natural membranes and in artificial devices by pressure-driven filtration through synthetic membranes (ultrafiltration). Volume homeostasis is especially critical for those with end stage renal disease (ESRD) as well as for those prone to congestive heart failure (CHF) in contrast to solute homeostasis which may be satisfactorily approximated by in-clinic treatments. Current devices in the art lack the ability to maintain volume homeostasis in a patient because they are unable to maintain continuous volume removal from a patient's bloodstream. Further, these devices operate without interruption only for relatively short intervals and require medical intervention which results in frequent trips to the clinic, which in turn interrupts their use.

Therefore, there exists a need for a device, system, and/or method for transferring some of the water content of blood from a patient's blood stream to a successor device in a coordinated, complete and safe manner. Such a device, system, and/or method would remove failure as a major cause of limited treatment times out of the clinic, and would provide other benefits, particularly the continuous maintenance of volume homeostasis.

SUMMARY

A wearable ultrafiltration apparatus is provided. The apparatus can include a first ultrafilter for filtering a patient's blood along a first fluid path and a second ultrafilter for filtering the patient's blood along a second fluid path. The apparatus can also include a valve that can be positioned in a first position for directing the patient's blood along the first fluid path. The valve can also be positioned in a second position for directing the patient's blood along the second fluid path. When the valve is in the first position, blood can flow along the first fluid path and prevent blood from flowing along the second fluid path. When the valve is in the second position, blood can flow along the second fluid path and prevent blood from flowing along the first fluid path. When the valve is in the first position, the second ultrafilter can be idle and can be serviced or replaced, and when the valve is in the second position, the first ultrafilter can be idle and can be serviced or replaced. Therefore, when an ultrafilter fouls, blood can be directed to the other ultrafilter while the fouled ultrafilter is being serviced or replaced.

In a first embodiment of the apparatus the valve can include a first pinch valve for directing blood along the first fluid path and a second pinch valve for directing blood along a second fluid path. The first fluid path and the second fluid path can converge at a Y connector before the patient's blood is returned to the patient. The first fluid path can include a third pinch valve for directing blood flow to the Y connector and the second fluid path can include a fourth pinch valve for directing blood flow to the Y connector. When the valve is in the first position, the first and third pinch valves can be in an open position to direct blood flow along the first fluid path and the second and fourth pinch valves can be in a closed position to prevent blood flow along the second fluid path. When the valve is in the second position, the second and fourth pinch valves can be in an open position for directing blood flow along the second fluid path and the first and third pinch valves can be in a closed position for preventing blood flow along the first fluid path. The first ultrafilter can include a first port for filtrate water disposal and the second ultrafilter can include a second port for filtrate water disposal. A battery operated pump can direct the patient's blood to the apparatus. The apparatus can include a waste container attached to the first port and the second port by a common outlet. The waste can be collected without the need for a waste pump. Both the first ultrafilter and the second ultrafilter can be microtubular membrane filters of a type used for hemodialysis.

In a second embodiment, the valve can include a rotatable rod assembly. The rod assembly can include a rod and a handle for rotating the rod from a first position to a second position. A first edge of the rod can direct the patient's blood to the first ultrafilter along the first fluid path. When the rod is in the second position, the first edge can be positioned in a second direction for directing the patient's blood to the second ultrafilter along the second fluid path. A second edge of the rod directs the blood from the first ultrafilter when the rod is in the first position or the second ultrafilter when the rod is in the second position. The rod can be rotated along a longitudinal axis.

In a third embodiment, the valve can include a spigot handle having a shaft operable to a first position and a second position. The first fluid path can include a first port for directing blood to the first ultrafilter and a second port for receiving blood from the first ultrafilter. The second fluid path can include a first channel for directing blood to the second ultrafilter and a second channel for receiving blood from the second ultrafilter. When the spigot handle is in the first position, blood flows through the first fluid path and when the spigot handle is in the second position, blood flows through the second fluid path.

A method of providing ambulatory ultrafiltration to a patient is also provided. The method includes the step of fitting an wearable ultrafiltration apparatus to a patient. The method further includes ultrafiltering said patient between hemodialysis treatments by passing the patient's blood through a first fluid path. The ultrafiltering step can also include detecting a fouling of an ultrafilter in the first fluid path and closing the first fluid path using a valve. The ultrafiltering step can also include replacing the fouled ultrafilter in the first fluid path with a new ultrafilter. The method can further include operating said valve to allow flow through a second fluid path to permit flow of blood through a second ultrafilter.

A method for maintaining volume homeostasis in a patient is also provided. The method includes the steps of providing a wearable ultrafiltration device including a first ultrafilter for filtering the patient's blood along a first fluid path, and a second ultrafilter for filtering the patient's blood along a second fluid path. The method also includes the step of drawing blood from the patient into the wearable ultrafiltration device at a predetermined continuous rate. The method further includes the step of directing blood to either one of the first ultrafilter or the second ultrafilter. The method includes the step of removing with water a specifiable plurality of small molecules from the patient's blood to create filtered blood. This specification is achieved through the design and operation of the ultrafilter. Still further, the method includes the step of returning the filtered blood back to the patient.

A pump for drawing a patient's blood into a device is also provided. The pump includes a first and a second tube containing the patient's blood positioned on opposing sides of the pump. The pump further includes a blade electrically operated by a motor and positioned between the first and second tubes. The pump further includes a first pusher plate positioned between the first tube and a first side of the blade, and a second pusher plate positioned between the second tube and a second side of the blade. When the blade rotates, the blade contacts the first pusher plate which contacts the first tube to release the patient's blood from the first tube, and thence in rotational sequence the blade contacts the second pusher plate which contacts the second tube to release the patient's blood from the second tube.

BRIEF DESCRIPTION OF THE DRAWINGS

The foregoing features of the disclosure will be apparent from the following Detailed Description, taken in connection with the accompanying drawings, in which:

FIGS. 2A-2D are diagrams illustrating a second embodiment of the wearable ultrafiltration device of the present disclosure;

FIGS. 3A-3D are diagrams illustrating a third embodiment of the wearable ultrafiltration device of the present disclosure;

FIG. 5 is diagram illustrating a fourth embodiment of the wearable ultrafiltration device of the present disclosure;

FIG. 6A is a top view of the wearable pump of FIG. 5;

FIG. 6B is a front view of the wearable pump of FIG. 5; and

DETAILED DESCRIPTION

The present disclosure relates to wearable ultrafiltration devices, methods, and systems, as discussed in detail below in connection with FIGS. 1-7.

Figure 1:
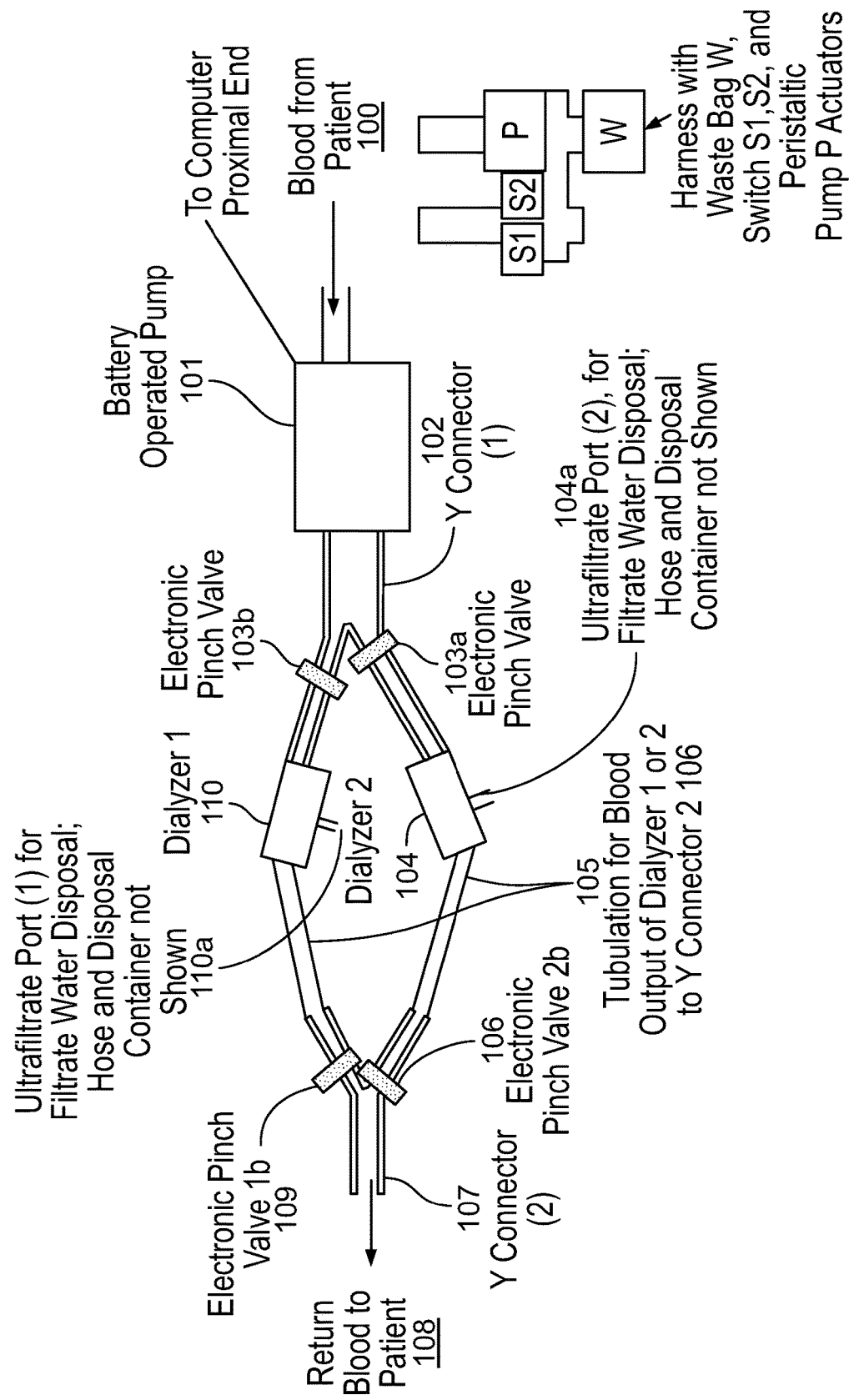
FIG. 1 is a diagram illustrating a first embodiment of the wearable ultrafiltration device of the present disclosure.

FIG. 1 is a diagram illustrating a first embodiment of the wearable ultrafiltration device of the present disclosure. FIG. 1 shows blood from a patient being drawn by a battery operated pump 101 and distributed to one of two ultrafiltration devices (e.g., ultrafilters). In particular, blood can be distributed to an ultrafilter 110 or an ultrafilter 104. It should be obvious to those skilled in the art that the device could easily be configured to accommodate three or more ultrafilters. The ultrafilters can be attached to a Y connector 102 where a pinch valve 103a and a pinch valve 103b can direct blood flow to the ultrafilter 104 and the ultrafilter 110. If it is needed for blood flow to be directed to the ultrafilter 104, then pinch valve 103a can be in the open position and the pinch valve 103b can be in the closed position. If it is needed for blood flow to be directed to the ultrafilter 110, then pinch valve 103b can be in the open position and the pinch valve 103a can be in the closed position. Once the blood is directed to either the ultrafilter 104 or the ultrafilter 110, it is then directed to a second Y connector 107. If blood is directed to the ultrafilter 104, then a pinch valve 106 can be in the open position. If blood is directed to the ultrafilter 110, then a pinch valve 109 can be in the open position. From the Y connector 107, blood returns to the patient through flow path 108.

As can be seen, the arrangement in FIG. 1 defines two fluid flow paths, one for the ultrafilter 104 and another for the ultrafilter 110. Initially, one fluid flow path and one ultrafilter can be selected for filtering a patient's blood. For example, ultrafilter 104 can be selected initially and pinch valve 103a can be open and pinch valve 103b can be closed. Moreover, the pinch valve 106 can be open and the pinch valve 109 can be closed. This directs blood flow to ultrafilter 104 and not to ultrafilter 110. When the ultrafilter 104 begins to foul, blood can be directed to the flow path for the ultrafilter 110. To switch flow paths, pinch valves 103a and 106 are closed and pinch valves 103b and 109 are open. This directs blood flow to the ultrafilter 110 (which is unused in this example) and away from the ultrafilter 104 (which has fouled in this example). While the ultrafilter 110 is filtering blood and that fluid flow path is selected, the ultrafilter 104 can be serviced or replaced so that when the ultrafilter 110 begins to foul, the fluid flow path can be switched back to direct blood flow to the ultrafilter 104. It should be noted that any fluid flow path can be selected first, and the other fluid flow path can be selected by opening the corresponding pinch valves and closing the pinch valves for the initially selected fluid flow path. The water taken out of the blood from the two ultrafilters empties freely into a receptacle via ultrafilter ports 104a and 110a. The output blood, 108, with a prescribed amount of its water content removed by way of the ultrafilters is returned to the patient. The sequence of operations of the valves as described can be determined by a microprocessor.

It should be noted that in this embodiment, a patient or the patient's caretaker or other user can control whether the pinch valves remain open or closed. Therefore, such a person can control the fluid path and the ultrafilter which is filtering the patient's blood. Moreover, in all embodiments, such a person can control any feature of the present disclosure (e.g. a valve) to change the direction of the fluid flow path from one ultrafilter to another.

Figure 2A:
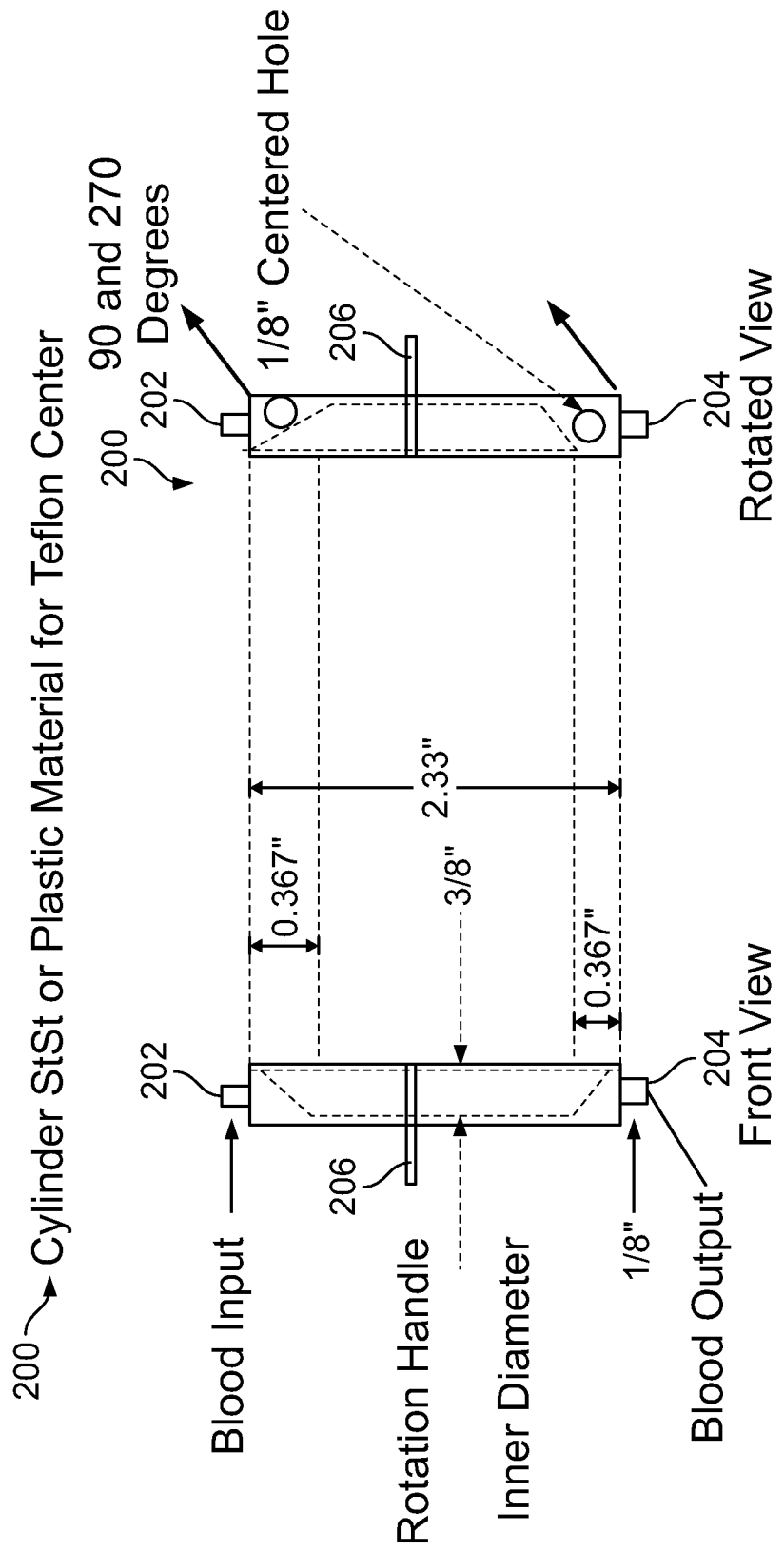

FIGS. 2A-2D are diagrams illustrating a second embodiment of the wearable ultrafiltration device of the present disclosure. The measurements shown in the drawings are for illustration purposes only and do not limit the scope of the present disclosure. FIG. 2A shows a front view and a rotated view, respectively, of a valve 200 for directing blood flow. The valve 200 includes a rod 214 (see FIG. 2b) as well as a blood input port 202, a blood output port 204, and a rotation handle 206. The rotation handle 206 changes the orientation of the rod 214 to direct blood flow from a first ultrafilter to a second ultrafilter. The rotation handle 206 is in a first position in the front view of FIG. 2A, and in a second position in the rotated view in FIG. 2A. When the rotation handle 206 is in the first position, blood can be directed to a first ultrafilter and when the rotation handle 206 is in the second position, blood can be directed away from the first ultrafilter and to a second ultrafilter. As discussed with respect to the first embodiment in FIG. 1, once the first ultrafilter begins to foul, the rod 214 can be rotated by the rotation handle 206 to direct blood flow away from the first ultrafilter which has fouled, to the second ultrafilter which can be unused. While the second ultrafilter is filtering blood, the first ultrafilter can be replaced or serviced so that when the second ultrafilter fouls, the rod 214 can be rotated by the rotation handle 206 to direct blood flow away from the now fouling second ultrafilter and to the newly-serviced or repaired/replaced first ultrafilter (path).

Figure 2B:
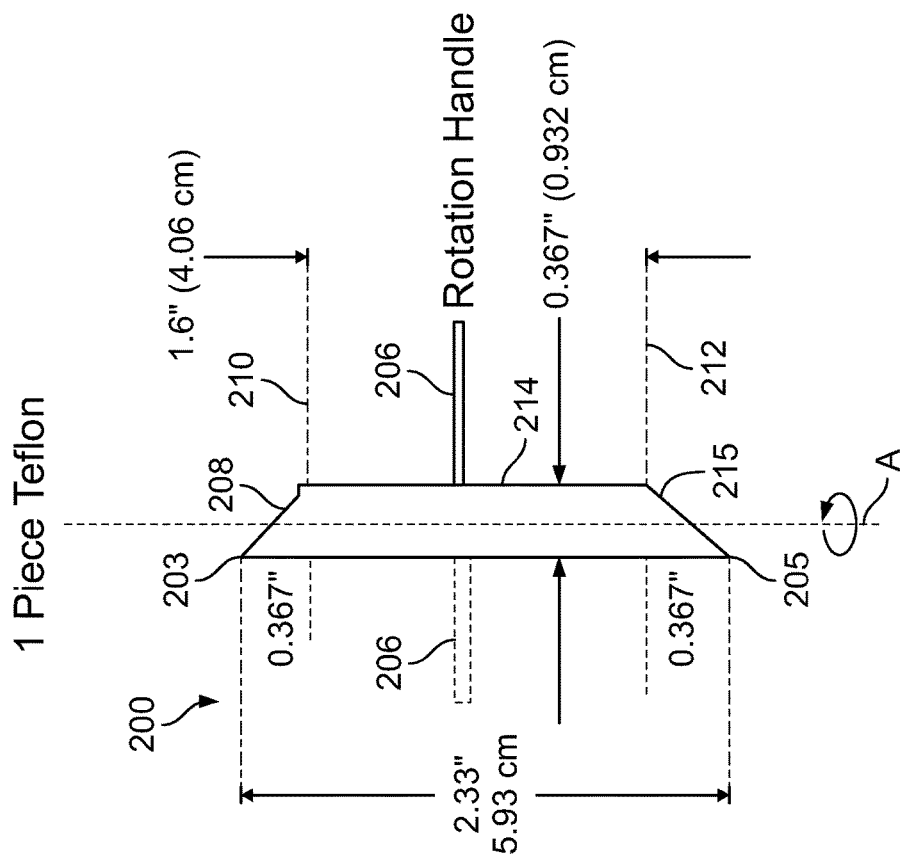

FIG. 2B shows a second front view of the valve 200 for directing blood flow. When blood reaches the rod 214 via a first port proximal to end 203, the blood can travel along a chamfered edge 208 to a flow path 210, which directs the blood to a first ultrafilter. After the first ultrafilter filters the blood, it can travel back along a path 212 and along a chamfered edge 214 and away from the rod 214 through a second port proximal an end 205. For illustration purposes, the rod 214 is shown in a first position as the rotation handle 206 is in a first position. However, the rod 214 can be rotated along a longitudinal axis A by moving the rotation handle 206 from a first position to a second position as shown in phantom in FIG. 2B. Rotating the rod 214 can direct blood flow to a second ultrafilter.

Figure 2D:
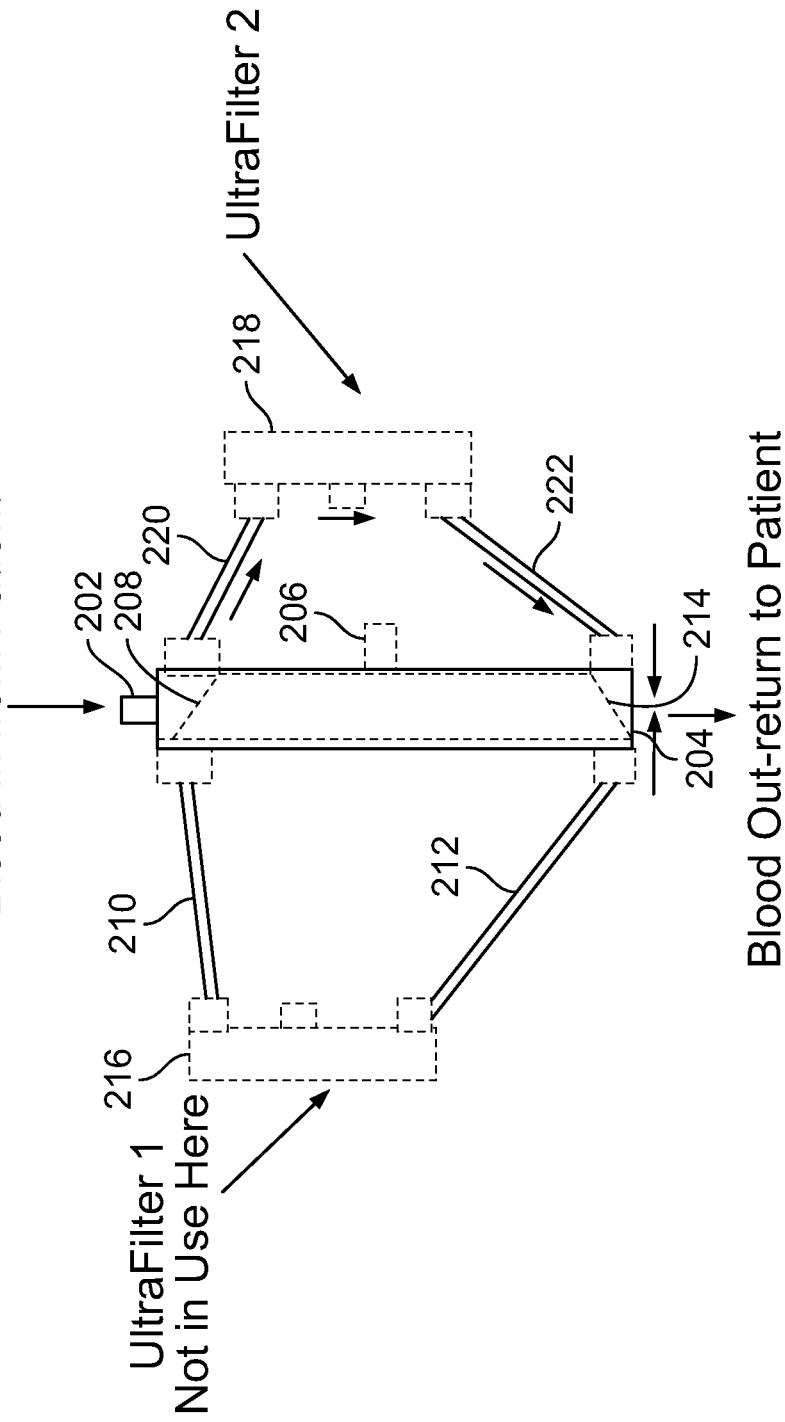

FIG. 2C is a diagram illustrating the second embodiment of the wearable ultrafiltration device when the rod 214 is in a first position. As can be seen, in this configuration, a fluid flow path is created to direct blood flow to a ultrafilter 216 and to prevent blood flow to ultrafilter 218. In particular, blood reaches the port 202 where it can travel along the chamfered edge 208 and along the flow path 210 to the ultrafilter 216. Then the blood will travel along the path 212 back to the valve 200 and along the chamfered edge 215 of the rod 214, where the blood will leave the valve 200 via the port 204. FIG. 2D is a diagram illustrating the second embodiment of the wearable ultrafiltration device when the rod is in a second position. As can be seen, in this configuration, a fluid flow path is created to direct blood flow to a ultrafilter 218 and to prevent blood flow to ultrafilter 216. In particular, blood can reach the port 202, travel along the chamfered edge 208, which is now oriented in a different position. The blood will then travel along the flow path 220 to the ultrafilter 218. After filtration by the ultrafilter 218, the blood will travel along the path 222 back to the valve 200 and along the chamfered edge 215 where the blood will leave the valve 200 via the port 204.

It should be noted that in this embodiment, a patient or the patient's caretaker or other user can control the position of the rod 214 and the rotation handle 206. Therefore, such a person can control the fluid path and the ultrafilter which is filtering the patient's blood.

The 4 flow-interrupters shown as pinch valves in FIG. 1 can be realized in a valve having a single rod in which flow paths are cut, encased in a close-fitting tube equipped with 6 ports closely coordinated to the cuts in the rod. The cuts in the rod direct an inflow to, and an outflow from, a primary processor (ultrafilter). When the rod is rotated the inflow to the primary processor is completely transferred to the successor processor and the connection of the outflow tube is connected to the outflow port of the successor processor, leaving the primary processor isolated from the continuing flow of blood through the system. A disposable blood circuit has multiple selectable blood circuit paths each has a pre-attached ultrafilter. The blood circuit has arterial and venous connectors for connection to a patient access, the arterial and venous connectors being connected to selectable branch portions to permit the flow of blood from the arterial connector, through a selected one of the selectable blood circuit paths and then to the venous connector. A harness has a peristaltic blood pump and switch actuators. The blood circuit is configured to be received by the blood pump and switch actuators to permit blood to be pumped through a selected one of the multiple selectable blood circuit paths. The switch actuators engage the selectable branch portions to permit the selection of either of the multiple selectable blood circuit paths.

The ultrafilters may include microtubular membrane filters of a type used for hemodialysis. The apparatus may include a pre-attached waste container attached to waste ports of the ultrafilter by a common outlet. The waste may be collected without the need for a waste pump. According to additional embodiments, the disclosed subject matter includes a method of providing ambulatory ultrafiltration to a patient. The method includes fitting apparatus as in any of the above claims to a patient, ultrafiltering said patient between hemodialysis treatments. The ultrafiltering includes passing the patient's blood through a first of said selectable blood circuit paths, detecting the fouling of an ultrafilter in said first of said selectable blood circuit paths, closing first of said selectable blood circuit paths using said switch actuators, and replacing a fouled ultrafilter with a new ultrafilter. The switch actuators may be used to open flow through a second of said selectable blood circuit paths to permit flow of blood through an unfouled ultrafilter.

Figure 3C:
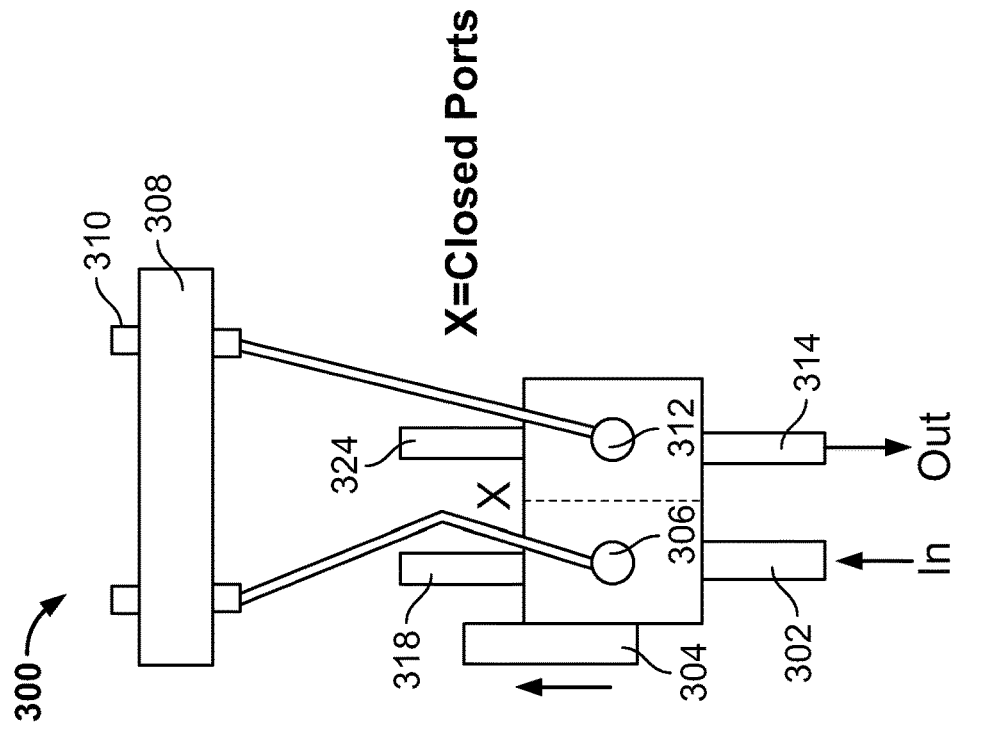

FIGS. 3A-3D illustrate another embodiment of the present invention. FIG. 3A shows a first configuration of a wearable ultrafilter 300. The wearable ultrafilter 300 has an input channel 302 where a patient's blood enters the wearable ultrafilter 300. When a spigot handle 304 is in a first position (as shown in FIG. 3A), blood flows from a port 306 to a first ultrafilter 308. Water exits the first ultrafilter 308 from a port 310. Blood exits the first ultrafilter 308 to the port 312. Blood then flows from the port 312 to the output channel 314 where it exits the wearable ultrafilter 300 and is returned to the patient. The handle 304 is in mechanical communication with a shaft 316, which simultaneously controls operation of the two stop cocks 317 illustrated in FIG. 3A. As shown in FIG. 3A, the handle 304 is in a first position which opens the stop cocks 317 to allow blood to flow through ports 306 and 312.

FIG. 3B shows a second configuration of the wearable ultrafilter 300. In this configuration, the blood enters the wearable ultrafilter 300 through the input channel 302. The spigot handle 304 is now in a second position which operates the shaft 316 and the stop cocks 317 to prevent blood from flowing through ports 306 and 312. Instead, blood will now flow to a channel 318 which directs blood to a second ultrafilter 320. When the first ultrafilter 308 requires service or replacement, the handle 304 can be operated from the first position shown in FIG. 3A to the second position shown in FIG. 3B to direct blood flow to the second ultrafilter 320. This permits no interruption-free for dialysis of a patient. Water exits the second ultrafilter 320 through the port 322. Blood flows from the second ultrafilter 320 to a channel 324. When the handle 304 is in a second position, port 312 is closed which allows blood to exit the ultrafilter 300 and return to the patient by flowing from channel 324 to channel 314.

Figure 3D:
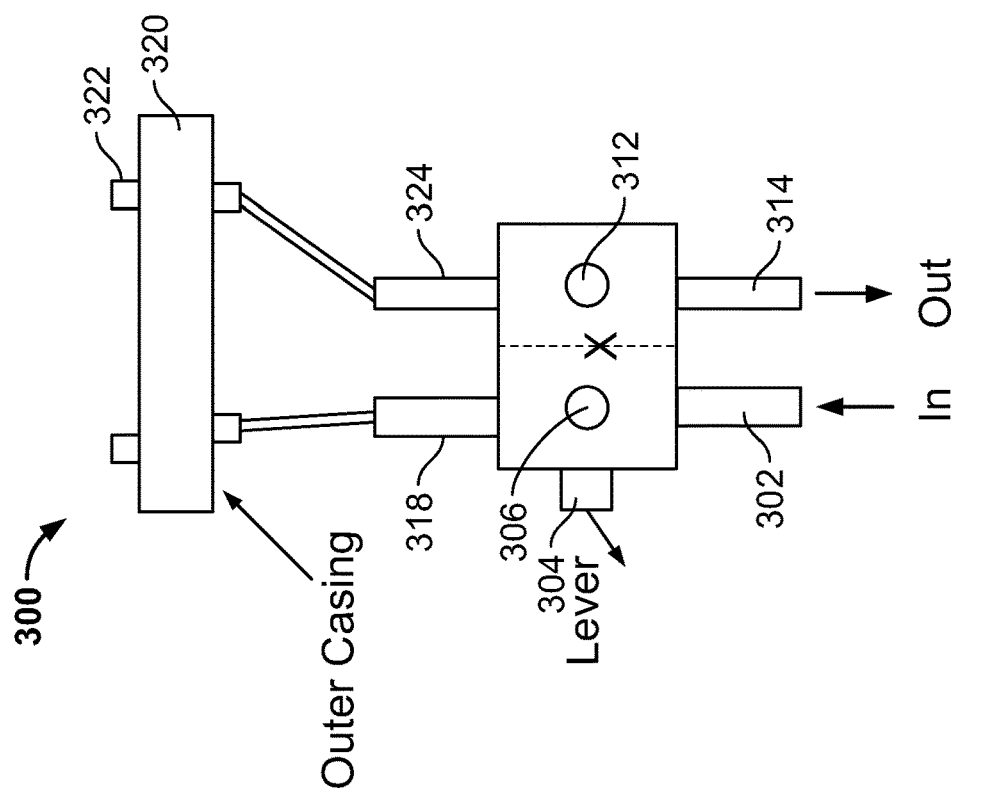

FIGS. 3C and 3D show another embodiment of the wearable ultrafilter 300, being operated with a four-way stopcock such that the handle 304 operates the four-way stopcock. FIG. 3C illustrates the wearable ultrafilter 300 in a first configuration and the handle 304 in a first position. FIG. 3D illustrates the wearable ultrafilter 300 in a second configuration and the handle 304 in a second position. With reference to FIG. 3C, blood enters the wearable ultrafilter 300: through the input channel 302. The spigot handle 304 is in a first position which operates the shaft 316 and the four-way stopcock to prevent blood from flowing through ports 306 and 312. Blood flows to a channel 318 which directs blood to the second ultrafilter 320. Water exits the second ultrafilter 320 through the port 322. Blood flows from the second ultrafilter 320 to a channel 324. When the handle 304 is in the first position, port 312 is closed, which allows blood to exit the ultrafilter 300 by flowing from channel 324 to channel 314, and returned to the patient. With reference to FIG. 3D, blood enters the ultrafilter 300 through the input channel 302. When the spigot handle 304 is in a second position, blood flows from the port 306 to the first ultrafilter 308. Water exits the first ultrafilter 308 from the port 310. Blood exits the first ultrafilter 308 to the port 312. Blood flows to the output channel 314 where it exits the wearable ultrafilter 300, and returns to the patient.

It should be noted that in this embodiment, a patient or the patient's caretaker or other user can control the position of the handle 304. Therefore, such a person can control the fluid path and the ultrafilter which is filtering the patient's blood.

All embodiments of the ultrafiltration apparatus can have an alarm or alert system for notifying the user, wearer, doctor, caretaker, etc. that it is possibly necessary to alter the device to direct blood flow from the currently used ultrafilter to the other ultrafilter. The ultrafiltration device can send a notification that it is time to switch from one ultrafilter to another. The ultrafiltration device can also send a notification that the system should be turned off due to an air bubble. Alternatively, the device can shut down automatically when detecting an air bubble. The ultrafiltration device can also send a notification that the battery is running low and provide the time remaining until the battery is exhausted, or to report the percentage of battery life remaining. Finally, the ultrafiltration device can send a notification that the pump is not working properly. The ultrafiltration device can have hardware to connect to the internet to send a notification via text message, email, etc. on any type of device such as a computer, PC, tablet, phone, etc.

Systems, methods, and/or device(s) for maintaining volume homeostasis in a patient will now be described in greater detail. The systems, methods, and/or device(s) can maintain volume homeostasis only, or can filter blood in conjunction with maintaining volume homeostasis. The methods for maintaining volume homeostasis can be carried out using any of the devices discussed in the present disclosure. In particular, a wearable device can be used to maintain volume homeostasis by patients with end stage renal disease (ESRD) requiring regular dialysis clinic visits (e.g., three times weekly) for waste product and additional volume adjustment. Similarly, the devices and accompanying methodologies are efficacious for use with patients suffering from congestive heart failure (CHF). In both sets of patients, the removal of excess volume is critical. Rapid removal of the volume retained in ESRD patients is primary significant cause of discomfort and pain endured by the patient during their dialysis treatments and contributes to hypertension and heart failure in these patients. Further, rapid removal of fluid volume during dialysis has been shown to impede removal of catabolites from, particularly muscle tissue.

For patients suffering from either ESRD or CHF, the present systems and methods and related devices discussed here are designed to eliminate retained volume by removing fluid at a constant, slow and regular rate. Accordingly, patients using the present systems and methods can reduce their clinical visits significantly. With the system operating continuously between clinic visits (e.g., 72-96 hours), the overall comfort of the patients' treatments will be greatly enhanced, blood pressure will be better controlled and episodes of severe fluid overload will be minimized.

The systems and methods (and related devices) for maintaining volume homeostasis include two ultrafilters selected (manually or automatically) by a switch such that one ultrafilter is in-use at any given time. Blood is pumped from the patient, passing through one of the two ultrafilters and returned to the patient using a small rechargeable battery operated pump. The ultrafiltrate removed from the blood is discharged into a plastic bag which the patient can empty periodically as needed. A similar procedure is followed for CHF patients.

To achieve a constant volume of homeostasis, the systems and methods utilize a miniature portable, wearable system (as described herein) utilizing the elements used in clinical dialysis, but as discussed herein operating continuously. The portable-wearable device can be attached to a halter, waist belt or specially constructed garment worn by the patient.

When treating patients with ESRD, it is highly desirable to remove toxic metabolites and maintain volume homeostasis. If volume (water and small molecules) is removed in a slow, continuous fashion, it stabilizes blood volume and blood pressure. It also avoids nervous reactions associated with cyclic disturbances of homeostasis.

The present disclosure provides a wearable ultrafiltration device (and corresponding systems and methods) used by a patient between dialysis visits. The device is designed to maintain body weight of a patient by slowly and continuously removing fluid. By maintaining a constant volume of homeostasis, there is a resulting reduction in the amount of times a patient has to visit a clinic. This also reduces a patient's discomfort while undergoing ultrafiltration and toxin removal by diffusion during dialysis. In particular, the device includes at least two ultrafilters, a switch, a pump, and an adjustable flow resistor connecting tubing and two blood access points. A patient's blood is pumped from the patient's body and passes through one of the two ultrafilters where ultrafiltrate from the filters is directed into a plastic bag which the patient can periodically empty. The patient's blood is then returned to the patient's body using a pump that is battery operated.

A wearable ultrafiltration apparatus for maintaining volume homeostasis includes a first ultrafilter for filtering a patient's blood along a first fluid path and a second ultrafilter for filtering the patient's blood along a second fluid path. The apparatus can also include a switch that can be placed into a first position to direct the patient's blood along the first fluid path. The valve (or switch) can also be repositioned into a second position to direct the patient's blood along the second fluid path. When the valve is in the first position, blood can flow along the first fluid path and prevent blood from flowing along the second fluid path. When the valve is in the second position, blood can flow along the second fluid path and prevent blood from flowing along the first fluid path. The switch can also be placed in a third position bypassing the ultrafilters and return blood to the patient. When the valve is in the third position, blood is prevented from flowing along the first and second fluid paths while flow is maintained through all other tubing units.

For patients suffering from ESRD, and for many with CHF, it is important to remove enough volume so the patient remains euvolemic. The wearable device (and systems/methods) of the present disclosure removes water by pumping blood from the patient through an ultrafilter and returning it to the patient after filtering, and performing this process continuously. The pump is powered by a battery that is rechargeable and exchangeable. The device extracts water from the blood. In particular, the device includes a mechanical resistor disposed after the distal end of an ultrafilter to maintain a sufficient transmembrane pressure within the ultrafilter to control the flowrate of filtrate that is removed from the patient's blood.

The wearable device includes two ultrafilters connected by a switch. The switch can direct a patient's blood to a first ultrafilter if, for example, a second ultrafilter is clogged or otherwise inoperable. The switch can also direct a patient's blood to the second ultrafilter if, for example, the first ultrafilter is clogged or otherwise inoperable. Alternatively, the switch can bypass both the first and second ultrafilters.

The device of the present disclosure can include two separate portions. First, a sterile package can include the ultrafilters, tubing, pressure transducer and switches (as explained in greater detail above). Second, a non-sterile structure can include a pump housing, a battery, a pump motor, and a pressure measuring terminus (which can be located underneath the pump mechanism). Periodically, the patient visits his/her respective kidney or heart clinic to have the device serviced, for example, by having the battery replaced and/or a new sterile package installed.

With regard to maintaining volume homeostasis, the systems, methods and devices provide continual, slow ultrafiltration of a patient suffering from ESRD and/or CHF or any other applicable disorder. The systems, methods and devices remove water, salt and other small molecules from the bloodstream on a continuous basis in small increments or amounts. Providing a continual and slow ultrafiltration portable device worn by the patient will ease the patient's pain and suffering caused by the removal of toxic waste and volume from standard dialysis treatments which tend to occur three times a week. By separating ultrafiltration from dialysis, the efficiency of the dialysis treatment is improved which reduces a patient's visits to a dialysis clinic and allows the clinic to accept additional patients. The wearable dialysis device runs continuously, halting only for required maintenance and during the time an ESRD patient receives regular dialysis at the clinic. In addition by using Bluetooth or other means of transmission, certain parameters of the wearable ultrafiltration process can be continuously monitored by the patient, caregiver, physician or clinic.

Figure 4:
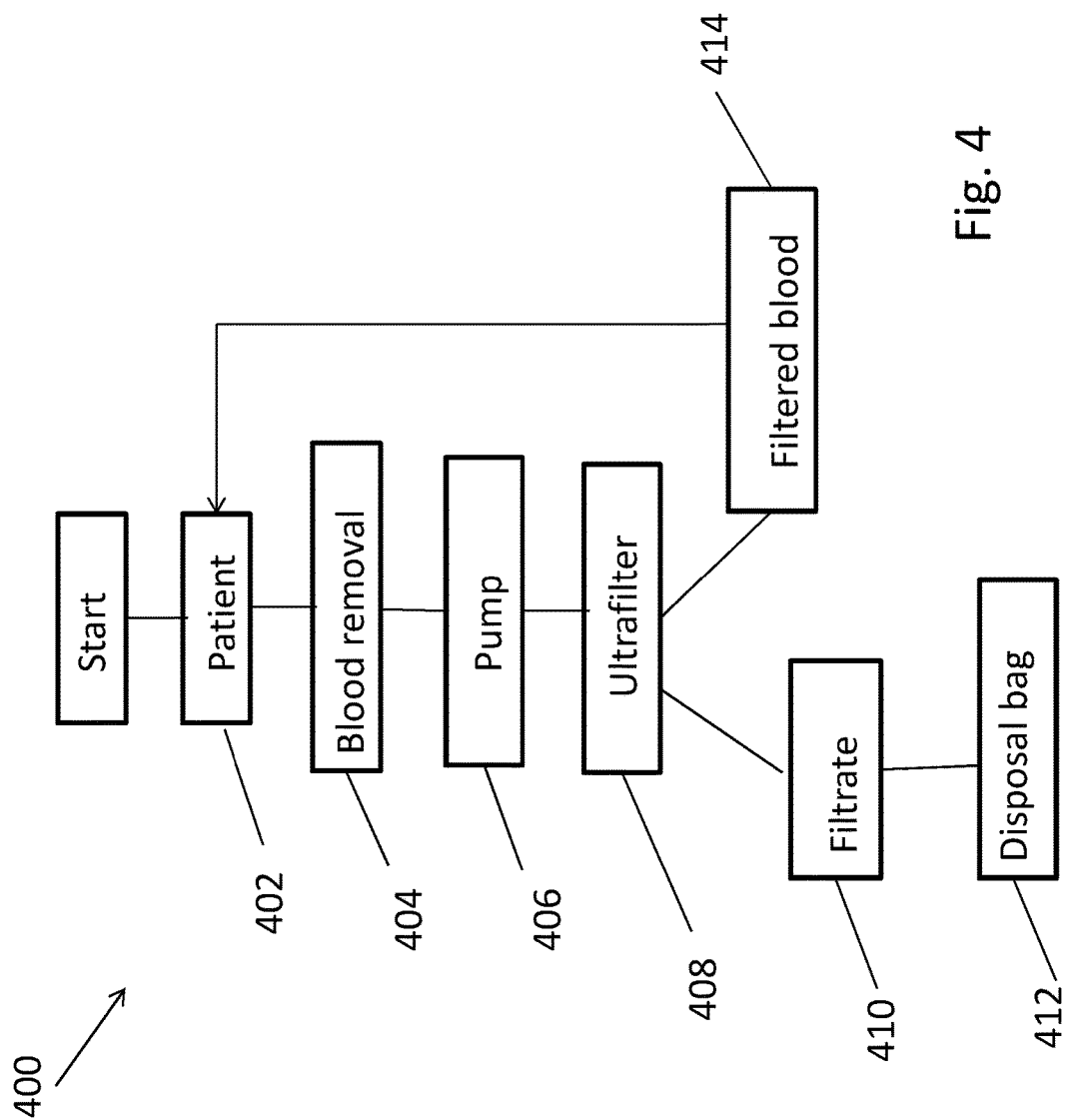
FIG. 4 is a flowchart illustrating a process for maintaining volume homeostasis in a patient.

FIG. 4 is a flowchart illustrating a process 400 for maintaining volume homeostasis in a patient. The process 400 removes volume from the blood slowly and continuously to maintain volume homeostasis in a patient. In step 402, a patient wears the device. Blood removal utilizes means for accessing an artery of the patient by any number of well-known means described in the literature. In step 404, the device removes blood from the patient. In step 406, a blood pump facilitates steady removal of blood from a patient. The pump can be powered by a rechargeable battery (or any other suitable battery), or it can be powered by a wired power source. The blood pump (which can be non-occlusive) can be controlled via Bluetooth by a remote device. The blood pump can maintain a steady flow of blood for as many hours as the battery needs to be replaced or charged. This constant, relatively slow removal makes it possible to achieve homeostasis of the patient between the times when the patient visits the clinic for dialysis. In step 408, the patient's blood leaves the pump and is directed to one of two ultrafilters, which filters the blood by taking out fluid that is mainly salt water. In step 410, the salt water leaves the ultrafilters as filtrate. In step 412, the filtrate flows into a disposal bag which can then be emptied by the patient. In step 414 (which occurs after step 408 in conjunction with steps 410 and 412), filtered blood emanating from the distal end of the ultrafilter is returned to the patient.

FIG. 5 illustrates a fourth embodiment of the wearable ultrafiltration device of the present disclosure. This embodiment can maintain volume homeostasis as described in the process of FIG. 4, but also any of the other embodiments described herein can also be used to maintain volume homeostasis in a patient in accordance with the process of FIG. 4 (and described elsewhere herein). As can be seen in FIG. 5, a patient 500 is fitted with a connector 502 having two connection points to a double lumen blood access catheter for drawing and returning blood. The blood is taken through sterile tubing 504 to the battery operated pump 506 leading to a Y connector section to enter either one of two ultrafilters 508a and 508b. The ultrafilters 508a and 508b can include (or even be formed from) hollow fibers encased in a tubular casing (which has the input and output ports for the blood and the filtrate and which can be formed from plastic). The battery of pump 506 can be rechargeable and provide a continuous charge for 72-96 hours, and even more depending on the battery or power connection used. The ultrafilter which receives the patient's blood depends on a position of a switch 510 which can be operated by the patient 500, or it can be operated by a remote device. The switch can operated automatically or manually. The switch can electronically operate a plurality of pinch clamps to close off a tube carrying blood to the ultrafilters in order to direct blood to either ultrafilter or to bypass them completely. A flow resistor 512 is used to increase the transmembrane pressure of either filter 508a or 508b. The flow resistor 512 is connected to both ultrafilters via the downstream Y connection. The filtered blood (e.g., blood with an amount of the salt water removed, as controlled by the flow resistor proceeds by way of passage through either ultrafilter 508a or 508b), returning to the patient via the second connection 514 of the double lumen blood access catheter. Having two ultrafilters greatly increases the probability of achieving a specified amount of filtration between clinic visits over that obtainable from a single filter. In the event clotting occurs in one of the two ultrafilters, the other ultrafilter can be used by operating the switch 510 so filtering remains continuous and uninterrupted. A Bluetooth pressure detector/transmitter 516 is located after the flow resistor 512. The device also includes a monitor to detect air and air bubbles in the blood, and the pump 506 can halt blood flow upon detection of a bubble. Patients using the device will not require anticoagulation.

FIG. 6A is a top view of the pump 506 of FIG. 5. Other existing pulsatile pumps can be used with the methods and devices of the present disclosure. FIG. 6A shows a top platform 602 of the pump 506 that provides a mounting plate for moving parts. These moving parts include two pusher plates 604 and a blade (propeller/plate pusher) 606. The blade 606 can be contoured and mounted on a motor spindle 608. During operation of the pump 506, the blade 606 rotates and contacts both pusher plates 604 simultaneously. This simultaneous contact causes the two pusher plates 604 to move in opposite directions towards respective opposite mounted soft tubing 610a and 610b. Upon sufficient rotational movement (e.g., as the blade becomes near normal incidence to the soft tubing 610a and 610b), engagement of the blade 606 (via the pusher plates) and both soft tubes 610a and 610b result in squeezing of the soft tubing 610a and 610b. This causes fluid (e.g., blood) to be forced out of the tubing in a direction obedient to a plurality of check-valves 612a-d mounted at both ends of the two sections of the soft tubing 610a and 610b. On further rotation of blade 606, the squeezing pressure is released forming a partial vacuum inside the soft tubing 610a and 610b, which causes blood from the patient to be forced/drawn into the soft tubing 610a and 610b. The squeezing and releasing of the pressure on the soft tubing 610a and 610b results in two pulses of fluid (e.g., blood) pumped for each 360 degree rotation of the blade 606.

FIG. 6B is a front view of the pump 506 of FIG. 5. This front view shows the ends of the two soft tubes 610 before the check valves 612a-d are mounted. This view also shows how the pusher plate 604 assist in creating a channel 614 for both soft tubes 610 to be mounted into the channel 614. The top platform 602 includes a first side 616 and a second side 618. A top plate with front and back side can be provided to enclose the entire structure. Inside the enclosure is a direct current (DC) motor 620, attached to the underside of the top platform 602. The motor spindle 608 fits through the top platform 602 while the blade 606 rests between the pusher plates 604. An additional top cover plate can be attached to top of channels 614 to provide complete covering of the pump 506.

Figure 7:
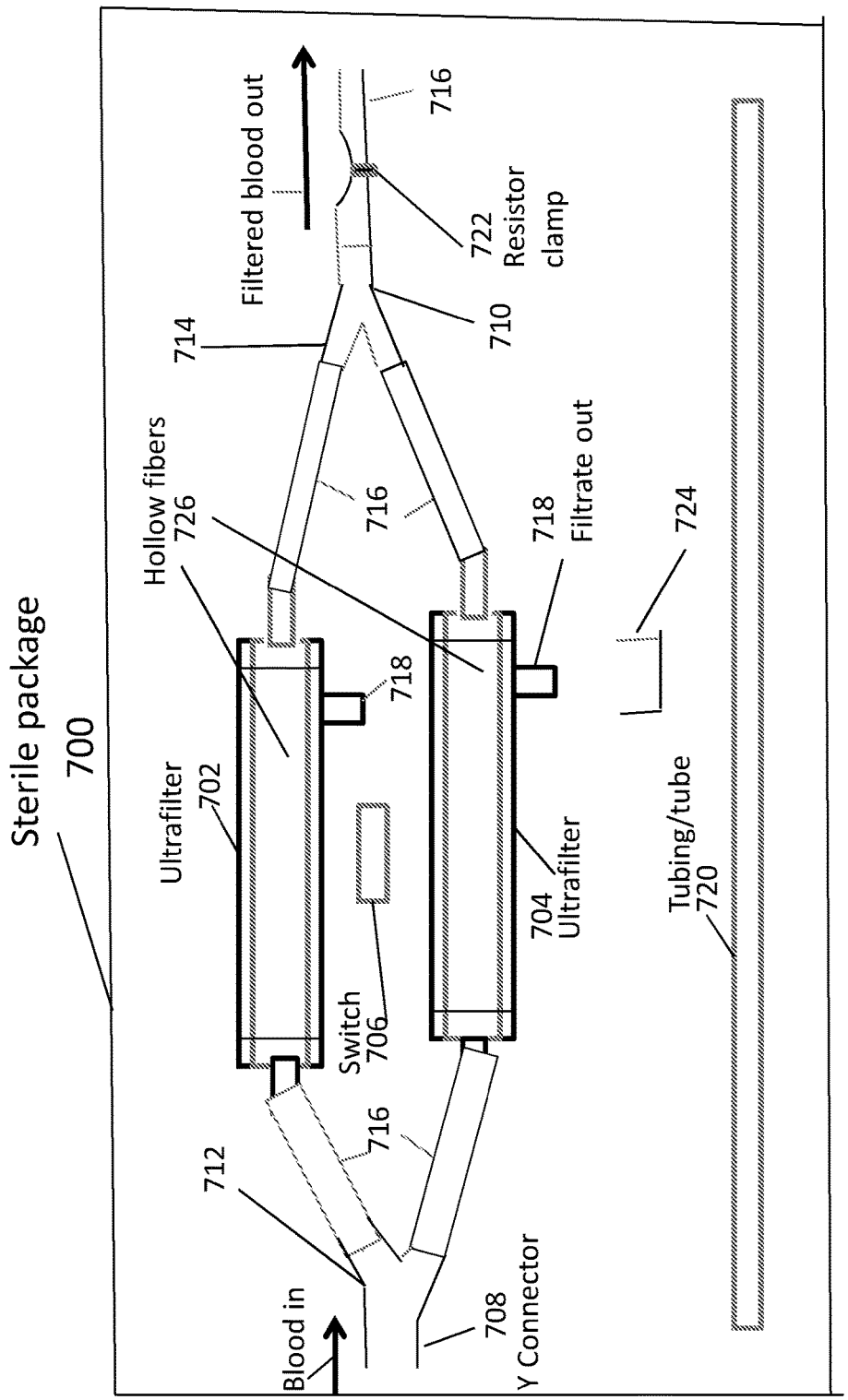
FIG. 7 is a diagram illustrating a sterile packaging for enclosing the wearable ultrafiltration device.

FIG. 7 is a diagram illustrative of a sterile packaging 700 for enclosing all components of the wearable ultrafiltration device that may be wetted by blood. As can be seen in FIG. 7, the sterile packaging 700 includes a first ultrafilter 702, a second ultrafilter 704, a switch 706, a first Y connector 708, a second Y connector 710, a first Y branch 712 and a second Y branch 714. A plurality of tubes 716 (which can be sterile and disposable) are used to transport blood throughout the device. As can be seen, the device in the packaging also includes input ports and output ports to the ultrafilters. Also included are filtrate output ports 718. Moreover, spare tubing 720 is also provided in the package 700. At the distal end, the straight section of second Y connector 710 is attached to a section of tubing with a constrictor or resistor clamp 722. As an example only, the resistor clamp 722 can be positioned between 0.5 to 2 cm from the end of the straight branch of Y connector 710. The resistor clamp 722 surrounds and clamps down on the tube, but it can also be in the form of a micrometer rod pushing on the tube with a calibrated amount of pressure determined by the Vernier scale on a micrometer. The resistor clamp 722 can control the pressure difference across the hollow fibers of the ultrafilters and the surrounding casing to produce filtrate of approximately 1-2 cc/min. The filtrate removed from the blood of a patient is an ultrafiltrate of plasma having water and dissolved small molecules at a concentration approximating what is in the patient's blood.

The pump 506 can also provide the pressure to draw blood from the patient through either one of two said ultrafilters between 25 and 50 cc/min and a filtration rate between 0.75 and 1.5 cc/min. The pump can also be set to pump blood at 25-40 mL/min from which the working filter forms a filtrate of 0.5-2 cc/min. Of course, other rates are possible.

The device in the sterile packaging 700 also includes a Bluetooth component attached to a pressure sensor connected in parallel to the output of the ultrafilters. The Bluetooth component includes a microcircuit which transmits the pressure data continuously and which can be detected by a smart device and transmitted to the internet for monitoring.

The pump 506 described above in connection with FIGS. 4-6 need not be included in the sterile packaging 700, as it can be affixed to the patient separately and apart from the device in the sterile packaging 700. This can allow the components of the device to be easily replaced or shipped or serviced. The sterile packaging 700 can include any of the devices described in the present disclosure.

Having thus described the system and method in detail, it is to be understood that the foregoing description is not intended to limit the spirit or scope thereof. It will be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure.

What is claimed is:

1. A wearable ultrafiltration apparatus, comprising:
   a first ultrafilter for filtering a patient's blood along a first fluid path;
   a second ultrafilter for filtering the patient's blood along a second fluid path; and
   a valve being positionable in a first position for directing the patient's blood along the first fluid path and being positionable in a second position for directing the patient's blood along the second fluid path;
   wherein when the valve is in the first position, blood flows along the first fluid path and is prevented from flowing along the second fluid path and when the valve is in the second position, blood flows along the second fluid path and is prevented from flowing along the first fluid path;
   wherein when the valve is in the first position, the second ultrafilter is idle and capable of being serviced or replaced, and when the valve is in the second position, the first ultrafilter is idle and capable of being serviced or replaced; and
   wherein the valve includes a rod including a handle attached thereto for rotating the rod from the first position to the second position, wherein the rod includes a first edge positioned in a first orientation when the rod is in the first position, the first edge directing the patient's blood to the first ultrafilter along the first fluid path, and wherein when the rod is in the second position the first edge is positioned in a second orientation for directing the patient's blood to the second ultrafilter along the second fluid path.

2. The apparatus of claim 1, wherein the first ultrafilter includes a first port for filtrate water disposal and the second ultrafilter includes a second port for filtrate water disposal, and wherein a waste container is attached to the first port and the second port by a common outlet.

3. The apparatus of claim 1, wherein a battery operated pump directs the patient's blood to the apparatus.

4. The apparatus of claim 1, wherein the first ultrafilter and the second ultrafilter are microtubular membrane filters of a type used for hemodialysis.

5. The apparatus of claim 1, wherein the rod includes a second edge for receiving the blood from the first ultrafilter when the rod is in the first position or the second ultrafilter when the rod is in the second position.

6. The apparatus of claim 5, wherein the rod is rotated along a longitudinal axis of the rod.

7. The apparatus of claim 1, wherein the valve comprises a spigot handle having a shaft operable to a first position and a second position and wherein when the spigot handle is in the first potion, blood flows through the first fluid path and when the spigot handle is in the second position, blood flows through the second fluid path.

\* \* \* \* \*